United States Patent [19]

Bremer et al.

[11] 4,215,696
[45] Aug. 5, 1980

[54] BIOMEDICAL ELECTRODE WITH PRESSURIZED SKIN CONTACT

[75] Inventors: Roger E. Bremer, Fort Lee, N.J.; Richard D. Falb, Bristol, Ind.

[73] Assignee: Graphic Controls Corporation, Buffalo, N.Y.

[21] Appl. No.: 890,630

[22] Filed: Mar. 20, 1978

[51] Int. Cl.³ .............................................. A61B 5/04
[52] U.S. Cl. ................................... 128/641; 128/803
[58] Field of Search ............... 128/2.06 E, 2.1 E, 404, 128/410, 411, 416, 417, 417 A, 418, DIG. 4, 639–641, 798, 802, 803

[56] References Cited

U.S. PATENT DOCUMENTS

| | | | |
|---|---|---|---|
| 3,027,333 | 3/1962 | Friedman | 128/417 X |
| 3,265,638 | 8/1966 | Goodman et al. | 128/417 A |
| 3,862,633 | 1/1975 | Allison et al. | 128/2.06 E |
| 3,901,218 | 8/1975 | Buchalter | 128/2.06 E |
| 3,945,384 | 3/1976 | Allison et al. | 128/2.06 E |
| 3,973,557 | 8/1976 | Allison | 128/2.06 E |
| 3,993,049 | 11/1976 | Kater | 128/2.06 E |
| 4,092,985 | 6/1978 | Kaufman | 128/417 X |
| 4,126,126 | 11/1978 | Bare et al. | 128/2.06 E |
| 4,137,909 | 2/1979 | Hix | 128/2.06 E |

OTHER PUBLICATIONS

*Nasa Tech Brief*, Nov. 1969, No. 69–10598, pp. 1 & 2, Supplemental pp. i, ii.

*Primary Examiner*—Lee S. Cohen

*Attorney, Agent, or Firm*—Michael G. Berkman

[57] ABSTRACT

A disposable biomedical electrode which includes a vaulted dome-like electrolyte-containing chamber or cavity bridged at its open bottom by a highly flexible and conformable microporous membrane, the latter being covered with an adhesively-secured protective film the film being strippable preparatory to adhesively securing the electrode to a body surface. The electrode material and shape are such that the vaulted housing is physically distortable upon downward pressure applied thereto, thereby to force the electrolyte to diffuse through the microporous membrane into positive and low-electrical-resistance contact with the skin surface of a subject. Concurrently, the internal volume of the electrolyte-containing chamber having been materially reduced, the housing maintains a positive, resilient, sustained pressure of electrolyte against the skin surface ensuring enhanced, low-impedance electrical continuity between the skin of a subject and the electrode terminal, thereby to minimize objectionable disruptive variations in signal strength, and to ensure instantaneous electrical response and rapid stabilization, enhanced through an improved electrode-electrolyte system. The electrode is further characterized in the utilization of a thixotropic electrolyte which simplifies manufacturing procedures and extends shelf life, and in the incorporation of a proteolytic agent and a surfactant in the electrolyte to improve electrical contact between the electrolyte and the signal-emitting body surface.

12 Claims, 6 Drawing Figures

U.S. Patent    Aug. 5, 1980    4,215,696
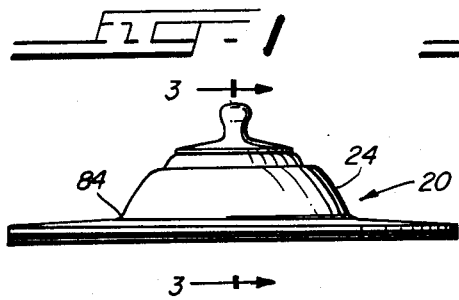
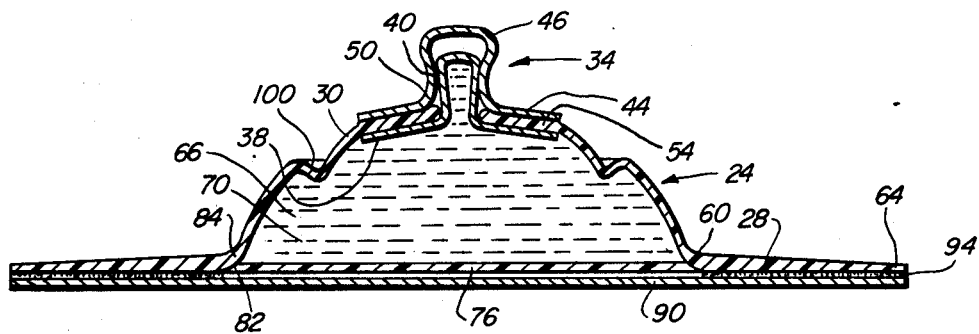
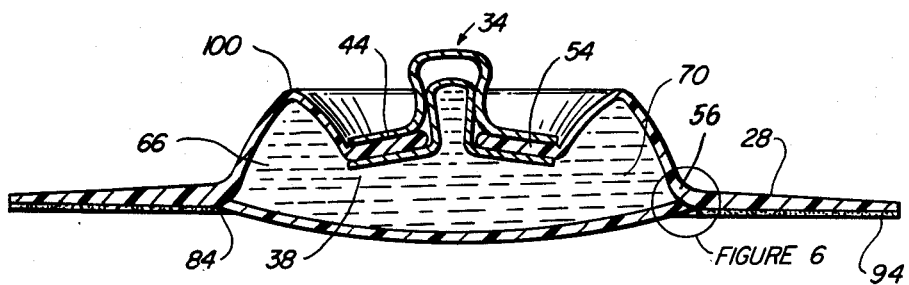
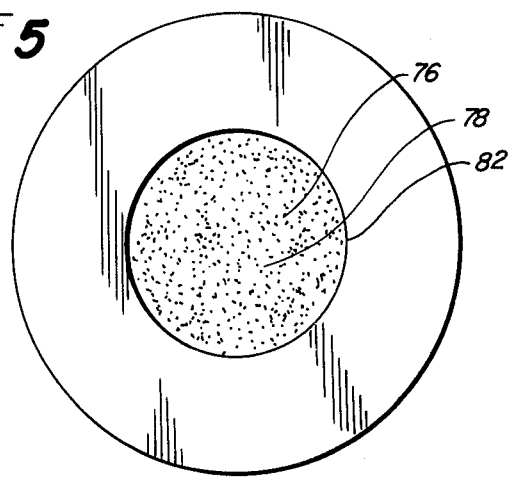
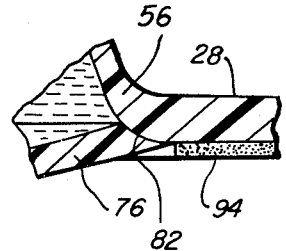

BIOMEDICAL ELECTRODE WITH PRESSURIZED SKIN CONTACT

BACKGROUND OF THE INVENTION

The prior art is replete with single-use, disposable biomedical electrodes. Extensive research and developement work conducted in this area, have resulted in electrodes of varied physical form and structural arrangement. In spite of such extensive investments in time and effort, no completely satisfactory electrode has evolved, each particular product having one or more inadequacies or objectionable features. For example, it has been a continuing challenge to devise an electrode assembly in which the contact of the conductive element of the electrode with the skin is established and maintained at a low impedance value with minimal motion artifacts or electrical noise. Another unrealized goal has been to achieve constant and maintain good electrical contact between the skin of a patient and the conductor portion of the electrode. Still another general aim of prior art researchers has been to produce such electrodes efficiently and at low cost. While many improvements have been made in disposable electrodes in recent years, the products heretofore available have fallen short of satisfying the stringent requirements of the medical profession. It is, therefore, the aim of the present invention to obviate shortcomings in the prior art devices and to provide an improved single-use, disposable electrode which satisfies not only the demanding standards of function and reliability but which may also be produced economically and efficiently to minimize cost.

The present invention relates to an improved biomedical electrode for application to a body surface. More particularly, the invention is directed to an electrode of the disposable type finding utility in detecting and in monitoring low level electrical signals at the skin of a patient.

SUMMARY OF THE INVENTION

It is a principal object of the invention to provide an electrode which ensures effective and sustained conductive contact, at low impedance, between the body surface and the terminal of the electrode.

A related important feature of the electrode of the invention is that it is readily and easily contoured to conform to the body surface contacted.

A very important feature of the invention is that it provides novel means whereby continuous and resiliently tensioned contact is maintained between the electrolyte of the electrode and the skin of a subject, thereby to ensure minimal electrical resistance at the interface of skin and electrolyte and to minimize electrical noise and motion artifacts.

Yet another feature of the invention is to provide an electrolyte composition, improved as to both physical characteristics and functional chemical ingredients.

In a preferred embodiment of the invention the electrolyte is a thixotropic composition facilitating the manufacture and assembly of the electrode. The electrolyte is convertible or transformable in use from a gel-like solid to an essentially fluid material, thereby to enhance the passage of the electrolyte through a microporous membrane interface to a skin surface to which the electrode is affixed.

Still another important feature of the improved electrolyte composition is the incorporation of a proteolytic agent or enzyme, this agent serving to "metabolize" or otherwise physically to remove any substantially inert proteinaceous material from the body surface to which the electrode is attached. The substantive effect is to facilitate establishment of a low resistance electrical conduction path between the body surface of the subject and a terminal of the electrode, through the electrolyte.

In accordance with a preferred embodiment of the invention the passage of the electrolyte through the retaining microporous membrane and the "wetting" of the skin surface by the electrolyte are enhanced by adding a surface active agent or surfactant to the electrolyte.

It is a feature of the invention that there is provided a microporous membrane which bridges or spans the open face of the electrode housing and retains the electrolyte in place. A protective film, which overlies the membrane, is removed and the electrode is then adhesively secured to the body surface, so that the microporous membrane is contiguously in contact with that surface.

A related feature of the electrode of the invention is that there is provided an improved interconnecting seal between the microporous membrane and the electrode housing, this seal being achieved preferably through ultrasonic welding.

Yet another important structural feature of the electrode is that the electrolyte-containing housing is integrally formed with a laterally extending annular flange, the latter having a transverse thickness gradient tapering from a greater thickness at its inner radial origin adjacent its juncture with the electrode housing to a lesser thickness at its outer radial terminus, thereby to provide physical strength, and stability of the electrode mounting flange and, concurrently, to enhance conformability of the flange to the body surface to which the electrode is applied.

Another feature of the invention is that the housing is formed with an integral ring-like bead delineating a mechanically strengthened annular zone in the region in which the terminal of the electrode is fastened to extend through the housing wall.

Other and further objects, features, and advantages of the invention will be evident from a reading of the following specification taken in conjunction with the drawings.

BRIEF DESCRIPTIONS OF THE DRAWINGS

FIG. 1 is a front elevational view of a biomedical electrode embodying the present invention;

FIG. 2 is a top plan view thereof;

FIG. 3 is an enlarged cross sectional view taken substantially on the lines 3—3 of FIG. 1 and illustrating the electrode of the invention prior to its securement to a body surface;

FIG. 4 is a cross sectional view similar to that illustrated in FIG. 3, but showing the configuration of the electrode after the housing has forcibly been pushed downward to establish tensioned pressure of the electrolyte with and against the body surface to which the electrode is secured;

FIG. 5 is a bottom plan view of the electrode of the invention, and

FIG. 6 is an enlarged fragmentary view of the zone identified in FIG. 4 and showing, schematically, the configuration at the juncture of the electrode housing with the semi-permeable membrane which bridges the opening at the base of the housing.

DESCRIPTION OF THE PREFERRED EMBODIMENT

The aims and objects of the invention are accomplished by providing, in a disposable electrode or monitoring device, a housing which is deformable under applied pressure to assume a new shape in which the volume of the electrolyte-containing cavity is reduced, pressurizing the electrolyte. The effect is resiliently to urge the electrolyte into positive electrically conductive contact with the body surface to which the electrode is fastened, thus to complete a low impedance electrical path between the body surface and the electrode terminal, through the interposed electrolyte. Additional important features of the electrode, including the thixotropic electrolyte and the proteolytic agent and the surfactant incorporated therein, further ensure the establishment of a reliable electrical path between the body surface and the electrode terminal.

Referring more particularly to the drawing, there is shown in FIGS. 1-5, for the purpose of illustrative disclosure, a preferred embodiment of the electrode of the invention, incorporating the teachings thereof. As best seen in FIGS. 1 and 3, the biomedical electrode 20 comprises an inverted, generally dish-shaped plastic housing 24 bounded by an annular, laterally extending flange or rim 28. The housing 24 has a vaulted dome-like roof 30 at the apex or center of which a terminal 34 is sealed to extend through the roof 30 to provide an electrically conductive path between the exterior of the housing 24 and its interior.

As illustrated in the cross-sectional view of FIG. 3, the terminal 34 constitutes a male snap fastener assembly consisting of a lower washer-like disk 38 with a central, integrally formed upwardly extending stud 40. The second snap fastener element is a surmounting flanged conductive cap 44 formed with an upwardly projecting downwardly opening stud receiving socket 46. To secure the terminal 34 to the roof 30 of the housing 24, the stud 40 of the lower component 38 is inserted upwardly to extend through an opening 50 at the apex of the roof 30 of the housing 24 and into the cooperating socket 46 of the cap 44. The two parts 38 and 44 are then forcibly pressed or crimped together to establish a mechanical interlock and to form a fluid-tight seal with the interposed plastic housing 24.

In the particular embodiment of the invention shown in FIGS. 3 and 4, the effectiveness of the seal between the roof 30 of the housing 24 and the terminal 34 is ensured by forming the upper extremity of the plastic housing with an integral, somewhat thickened ring-like annular bead 54. The bead 54 is embraced on its opposed lower and upper surfaces by the sandwiching annular flanges of the disk and cap 38 and 44 of the snap fastener assembly 34, the bead 54 delineating a mechanically strengthened, compressible zone.

An additional structural refinement in the preferred embodiment of the electrode housing 24 shown in FIG. 3 is that the integral annular flange 28 at the base 56 of the housing is formed with a transverse thickness gradient tapering from a greater thickness at its inner radial origin 60 adjacent its juncture with the vaulted housing wall to a lesser thickness at its outer marginal terminus 64 thereby to provide physical strength, rigidity and stability in conjunction with enhanced conformability of the flange 28 to the body surface (not shown) to which the flange 28 is ultimately adhesively secured.

The cavity 66 within the domed housing 24 is filled with an electrolyte composition 70, the latter serving its conventional role of establishing and maintaining electrical continuity between the skin surface to which the electrode is secured and the terminal 34 exteriorally of the electrode 20.

The electrolyte 70 may contain any preferred aqueous salt system including alkali metal and alkaline earth metal salts, ammonium salts, and ionizable organic salts. The electrolyte composition may be formulated to include water soluble or dispersible thickeners or resins such as carboxymethylcellulose, polyvinyl alcohols, hydrophylic polyacrylic acids and gums, so as to provide a viscous aqueous mass. In accordance with the present invention the electrolyte is a thixotropic gel convertible to a flowable fluid-like composition upon physical disturbance, as through pressure applied thereto. That is, the electrolyte which is a "solid" under dormant or storage conditions is transformed into a liquid when putting the electrode to use. Typical thixotropic agents finding utility in the practice of the present invention include "Cabosil" and "Syloid" sold by the Cabot Corporation, and "Acryloid" sold by Rohm & Haas.

As a further improvement to enhance the operation of the electrode, including the establishment of better electrical contact between the electrolyte and the skin surface, the electrolyte formulation includes a surface active agent (surfactant) or wetting agent, such materials being well-known in the art, and including anionic, cationic and non-ionic types.

It is an important feature of the invention that the open face of the electrode housing 24 is bridged by a microporous membrane 76 in which the openings 78 are exceedingly small but large enough to permit fluid passage therethrough, for example, under the application of slight pressure. A perforated plastic sheet material sold by Celanese Plastics Company under the trademark "CELGARD TYPE 2400" has been found suitable for the described purpose. While the membrane 76 itself may be secured to the housing 24 by any of several techniques including adhesive bonding, in a preferred embodiment of the invention the membrane 76 is bonded ultrasonically to provide a ring seal 82 at the juncture 84 of the housing wall 24 with the horizontally extending flange 28. The interjunction of the flange 28 with the housing 24 is microconvoluted or knurled, a configuration which facilitates the ultrasonic bonding of the membrane 76 to the flange 28 and ensures a positive, fluid-tight seal.

In order that the assembly be storage stable, and so that it can be shipped and handled without leakage, a peelable sheet or film 90 is provided which covers and temporarily seals the microporous membrane 76. The cover film 90 is secured on the undersurface of the surrounding annular flange 28 by an interposed pressure-sensitive adhesive 94. It is this same adhesive, exposed upon stripping of the protective film 90, that serves to anchor the electrode assembly 20 firmly in place on a skin surface of the subject.

As described, the chamber or cavity 66, defined by the microporous membrane 76 in conjunction with the housing 24 of the electrode, is completely filled with the electrolyte 70. A very important feature of the invention is that there is provided a novel housing structure and a method whereby, after removing the protective cover film 90 and fastening the electrode assembly 20 adhesively to the skin surface of a subject, positive and sustained electrical contact and low impedance electrical continuity between the electrolyte 70 of the electrode assembly 20 and the skin surface, through the microporous membrane 76, is achieved and maintained. In accordance with the practice of the invention, novel mechanical means are provided whereby the fluid-like electrolyte 70 in the chamber or cavity 66 of the electrode may be pressurized in use so that electrolyte 70 passes through the micropores 78 in the membrane 76 and resiliently and firmly maintains a sustained positive pressure against the skin surface to ensure low resistance electrical continuity between that surface and the terminal 34 of the electrode, through the electrolyte 70. The mechanism whereby this pressurization is achieved will be explained with reference to FIGS. 3 and 4.

As assembled and prior to actual use of the electrode, the housing 24 of the electrode is vaulted upwardly to define a generally dome-like cavity interior of the electrode assembly. As best seen in FIG. 3, the housing wall is scored or formed with an offset band or an inflection which extends as a circumambient, ring-like transformation zone 100 annularly about the housing. The zone generally parallels a plane defined by the microporous membrane 76. The transformation zone 100 functions as a mechanical "discontinuity" in the housing wall. For example, the housing wall acts as if weakened in the area indicated. That is, with the electrode adhesively secured in place on the skin surface of a subject, the application of downward pressure, as for example finger pressure, to the vaulted roof of the housing at the center or terminal 34 causes the dome-like roof of the housing to be displaced downwardly and inwardly to assume a new stable configuration, as illustrated in FIG. 4. The flexure zone 100 is then located at an upper edge of the now toroidal housing. An important effect of this mechanical transformation is materially to reduce the internal volume of the cavity 66 in which the electrolyte 70 is contained thereby forcing the electrolyte through the pores 78 of the microporous membrane 76 and into positive and direct pressurized contact with the skin surface of the subject. The mechanical shift of the housing wall is somewhat analagous to a "toggle" phenomenon, since the depressed disposition of the roof of the housing constitutes a new stable orientation whereby the established pressure system is maintained as a continuing state to provide an extremely stable conductive path between the body surface of the subject and the terminal 34 of the electrode assembly, through the electrolyte 70.

The particular mechanical configuration or contour of the housing depicted in FIGS. 3 and 4 is merely illustrative of the principle of the invention and is not to be construed as limiting the invention in any way, since, on the basis of the present disclosure, other mechanical arrangements for accomplishing the same purpose will be evident to those skilled in the art.

Upon a consideration of the foregoing description, it will be appreciated that there has been provided a simple yet highly effective disposable biomedical electrode in which cooperating and interrelated structural components have been combined in a novel arrangement. The resultant article is operative to achieve important goals not heretofore realized. While certain structural materials are preferred, including, for example, polypropylene for the housing of the electrode, and high conductivity metal for the terminal of the electrode, other plastics and other conductors may be used. For example, the terminal itself may conveniently consist of plastic elements coated with metallic conductive films or vacuum deposits. Additionally, preferably, the housing is fabricated by injection molding. It is contemplated that other manufacturing methods such as vacuum forming may be used. Again, whereas a preferred technique is to bond the microporous membrane to the housing through applied ultrasonic energy, an acceptable alternative technique is to use adhesives.

Many combinations of electrode materials and electrolyte media have been used in prior art electrode structures of the general type involved in the present invention. Although many of the materials described would be suitable in the present electrode, in accordance with the present invention specific novel combinations and formulations are preferred. These include $Zn/Zn^{++}$ and $Ag/AgCl$ couples. The electrolyte for the $Ag/AgCl$ system constitutes 0.14 M NaCl buffered at a pH of 7.3 with 0.01 M $Na_2HPO_4$, this buffer system being compatible with skin in that it has a similar ionic strength and pH. For the $Zn/Zn^{++}$ coupled an electrolyte containing $Zn^{++}$ in a concentration of about 0.1 M is suitable, a preferred electrolyte salt being 0.1 M Zn $(OAc)_2$ adjusted to a pH of about 6.0, using phosphate buffered saline. In order to obviate the development of fungal and bacterial growth after long term storage, a topical antiseptic, e.g. 4-chloro-3,5-xylenol was added to the electrolyte at a concentration of 0.033 percent. Many other antiseptic agents suitable for this purpose will occur to those skilled in the art.

Certain additional background material is believed to be helpful to ensure a full appreciation of the electrode of the present invention. For example, the detection of electrical signals emanating from the heart at the surface of skin generally falls into four modes:

a. Heart function monitoring e.g., as related to emergency circumstances, during surgery, or during a period of recovery from an episode. In the former two, the period of use is relatively short, and the electrode would be conveniently disposed of. In the recovery application, the patient's condition is monitored over several days or longer. The electrodes frequently dry out, become detached, or have to be replaced. These applications generally use from one to three electrodes. They are concerned with gross signals of amplitude, rate and uniformity, particularly to be warned of indicated heart arrest or arrhythmias. Convenience calls for disposable elements, and in the circumstances costs are not paramount.

b. Classical clinical electrocardiograms (EKG's)

These are generally designated as "scalar" or 12 lead EKG's. Occasionally the Frank/vector EKG is used, but the objectives are similar. This is a one-time encounter lasting around 10 minutes. At present, the most popular approach is to use plates and "Welch" suction caps, which have to be carefully affixed and maintained. This procedure involves skin preparation, application of gel, affixing electrodes securely, checking for adequate signals, cleaning electrodes and patient, and storing and maintaining electrodes. In addition to the hazard of cross-contamination, this seemingly archaic procedure is costly, and it lacks precision and uniformity. Yet it apparently is less expensive than using presently available disposable electrodes. Moreover, the clinical EKG requires more precision in its signals, since it is used for expert diagnosis and interpretation. Present disposables do not meet the standards of refinement, uniformity and consistency required.

C. Computer-aided electrocardiography

This technique employs a computer to process signals to aid the physician. One of the major advantages is more precise and uniform diagnosis which obviously requires very accurate and uniform signals. There is increasing interest in using these EKG's for comparative purposes both for the patient and against standards. Here again, precision and uniformity are required. Further new applications of this technique are emerging from the features of microcomputers. Again, requirements are precision and uniformity and good economies.

D. Advanced scientific applications

Heart signals used for isopotential body mapping, epidemiological studies; in conjunction with ultrasonics and other advanced diagnostic techniques, and a host of other research applications—all will require precision, uniformity and low costs.

The electrode of the present invention meets the needs of all four of the above application modes with a single high quality, low cost disposable product, directed toward making a functional and economic contribution in gaining better understanding of the heat function, better techniques of prevention and early detection of disease, selection and monitoring of therapy, and monitoring the patient when a crisis occurs in dealing with this country's number one killer.

Factors which are believed to contribute to the efficacy of the electrode described herein include a unique combination of design concept, which permits better performance, as well as economical manufacturing techniques. The electrode structure lends itself to existing production methods ensuring high quality products at low cost. For example, the disclosed procedure for sealing the connector into the housing permits filling the housing from the open bottom side, permits simple tooling for multiple connector assembly. The electrode structure permits the use of multiple cavity injection molds for housing in "egg crate" configuration, as well as accurate balance of connecting offal material in a balanced recycling formula. The configuration, plus thixotropic gel, permits rapid multiple, simultaneous filling of the cavities, and easy surface cleaning to facilitate bonding. The membrane material can be wound on a reel to use its directional stength to permit minimum webbing, thus reducing material cost but permitting tautness to facilitate rapid processing. In this position, ultrasonic sealing can be achieved by reversal of the conventional position of the horn and anvil, thereby permitting the filling position described above. At this same station, housings can be ultrasonically separated into individual units, which are then hand-inspected and enclosed with a protective cover. This procedure minimizes the manpower, provides good line balance and high speeds, with relatively low tooling costs. This assures good economics with uniform high quality.

In combination, the electro-chemical, physical properties and low material and production costs provide a highly efficient, low cost, disposable electrode, suitable because of these features for all four modes of physiological electrical signal processing.

Accordingly, while the disclosure is of a preferred embodiment of the invention, and while there has been provided a description of preferred methods and materials for assembly and fabrication of the electrode of the invention, it is apparent that numerous modifications and variations in structural detail, materials and in manufacturing techniques may be made without departing from the underlying principles of the invention. It is, therefore, desired by the following claims to include within the scope of the invention all such variations and modifications by which substantially the results of this invention may be obtained through the use of substantially the same or equivalent means.

What is claimed is:

1. A single use disposable biomedical electrode for use on a subject for receiving body-generated electrical signals at a body surface of the subject, said electrode comprising:

an inverted, generally dish-shaped housing having a vaulted dome-like roof, a base, and an integrally-formed, laterally extending annular flange at said base, said housing presenting a downwardly directed opening bounded by an inward edge of said flange, a microporous, fluid-permeable membrane, means securing said membrane to said housing at said base, whereby said membrane covers the opening in said housing, said membrane defining, in conjunction with said housing, a chamber for an electrolyte, tissue-compatible electrolyte means substantially filling said chamber, a peelable, fluid-impervious, protective cover film overlying said membrane and said flange, pressure-sensitive adhesive means releasably securing said film to said flange, electrically-conductive terminal means sealed to and extending through said roof of said housing and providing electrically-conductive communication between the exterior of said housing of said electrode and said electrolyte means contained within said chamber, said protective film being selectively removable to expose said adhesive means to facilitate securement of said electrode to a body surface through said adhesive means, and a ring-like transformation zone circumscribing said housing at a height intermediate upper and lower limits thereof, said zone extending in a plane generally paralleling said fluid-permeable membrane and functioning as a mechanical discontinuity and weakened portion of the wall of said housing, said vaulted roof of said housing being displaceable downwardly in response to pressure applied thereto to deform said housing at said transformation zone, thereby reducing the volume of said chamber containing said electrolyte means, resiliently pressurizing said electrolyte means contained in said chamber, and stressingly urging said electrolyte means to pass through said porous membrane and establishing positive electrically conductive contact with a body surface thereberneath, thereby completing and maintaining a sustained and stable conductive path between the body of the subject and said terminal means of said electrode.

2. The electrode as set forth in claim 1 wherein said means securing said microporous membrane to said housing comprises an ultrasonically produced ring seal.

3. The electrode as set forth in claim 1 wherein, at an interjunction of said flange with said vaulted housing, said flange defines a knurled configuration, thereby facilitating ultrasonic bonding of said flange to said membrane and a positive fluid-tight seal therebetween.

4. The electrode as set forth in claim 1 wherein said flange is formed with a transverse thickness gradient tapering from a greater thickness at its inner radial origin adjacent its juncture with said housing to a lesser thickness at its outer marginal terminus, thereby to provide physical strength, rigidity, and stability of said flange and, concurrently, to enhance contiguous physical conformability of said flange to a support body surface to which said flange is adhesively secured.

5. The electrode as set forth in claim 1 wherein said electrolyte means includes a surfactant to reduce surface tension at an interface of said electrolyte means with said microporous membrane, facilitating passage of said electrolyte means therethrough, and enhancing effective wetting of the body surface at a zone of securement of said electrode thereto.

6. The electrode as set forth in claim 1 and further comprising an integrally formed annular ring-like bead at said roof of said housing,
said bead delineating a mechanically strengthened center zone in said housing, and
wherein said terminal means of said electrode is sealed into and secured to said housing at said bead.

7. The electrode as set forth in claim 1 wherein said terminal means includes zinc and wherein said electrolyte means includes $Zn(OAc)_2$ as an electrolyte salt.

8. The electrode as set forth in claim 1 wherein said terminal means includes silver and wherein said electrolyte means includes sodium chloride.

9. The electrode as set forth in claim 1 wherein said electrolyte means includes a topical antiseptic.

10. In a single use disposable biomedical electrode for use on a subject for receiving body generated electrical signals at a body surface of the subject,
said electrode including:
an inverted, generally dish-shaped housing having a base, a vaulted dome-like roof, and an integrally-formed laterally extending annular flange at said base,
said housing presenting a downwardly directed opening bounded by an inward edge of said flange,
a microporous, fluid-permeable membrane, means securing said membrane to said housing at said base thereof, whereby said membrane covers the opening in said housing,
said membrane defining, in conjunction with said housing, a chamber for an electrolyte,
tissue-compatible electrolyte means substantially filling said chamber,
a peelable, fluid-impervious, protective cover film overlying said membrane and said flange,
pressure-sensitive adhesive means releasably securing said film to said flange,
electrically-conductive terminal means sealed to and extending through said roof of said housing and providing electrically-conductive communication between the exterior of said housing of said electrode and said electrolyte means contained within said chamber,
said protective film being selectively removable to expose said adhesive means to facilitate securement of said electrode to a body surface through said adhesive means, and
the improvement comprising a ring-like transformation zone circumscribing said housing at a height intermediate upper and lower limits thereof, said zone extending in a plane generally paralleling said fluid-permeable membrane and functioning as a mechanical discontinuity and weakened portion of the wall of said housing, and wherein said vaulted roof of said housing is displacable downwardly in response to pressure applied thereto to deform said housing at said transformation zone, thereby reducing the volume of said chamber containing said electrolyte means, resiliently pressurizing said electrolyte means contained in said chamber, stressingly urging said electrolyte means to pass through said porous membrane establishing positive electrically conductive contact with a body surface therebeneath, and completing and maintaining a sustained and stable conductive path between the body of the subject and said terminal means of said electrode.

11. The improvement as set forth in claim 10 wherein said electrolyte means is a thixotropic medium and constitutes a gel-like material convertible to a flowable fluid-like composition upon physical disturbance thereof, including pressure applied thereto, whereby said electrolyte means is a stable gel-like solid in storage and converts to a fluid when said electrode is put into use.

12. In biomedical procedures, a method of detecting electrical signals at a body surface of a subject and conducting such signals to a terminal of an electrode applied to the body surface, which method comprises:
placing against a body surface an electrode assembly having a vaulted downwardly-open, dish-like housing having an annular rim-like flange,
said housing having an electrically conductive terminal sealed in and extending through said housing,
adhesive means coating an undersurface of said flange,
gel-like electrolyte means filling said housing,
a microporous membrane sealed to and across said housing at a base thereof,
said membrane bridging the opening in said housing and serving to restrain said electrolyte means therewithin,
firmly pressing said electrode assembly into positive contact with the body surface about said flange, adhesively to bond said flange to the body surface through said adhesive means,
pressing downwardly upon said housing physically to transform said housing to assume a lower profile with a resultant reduced internal volume for said housing,
thereby to establish positive, sustained, tensioned pressure upon said electrolyte means and to urge said electrolyte means through said membrane to contact and to coat the body surface and to establish effective, minimal resistance, direct and substantially uninterrupted electrical contact with the body surface covered by the electrode assembly, and to provide reliable and reproducible electrical continuity between the body surface and said electrode terminal through interposed said electrolyte means.

* * * * *